(12) United States Patent
Tittelbach et al.

(10) Patent No.: US 8,062,352 B2
(45) Date of Patent: Nov. 22, 2011

(54) IMPLANTABLE DEVICE

(75) Inventors: Michael Tittelbach, Nuremberg (DE); Amir Fargahi, Buelach (CH)

(73) Assignee: Biotronik VI Patent AG, Baar (CH)

( * ) Notice: Subject to any disclaimer, the term of this patent is extended or adjusted under 35 U.S.C. 154(b) by 170 days.

(21) Appl. No.: 12/481,218

(22) Filed: Jun. 9, 2009

(65) Prior Publication Data
US 2009/0312833 A1 Dec. 17, 2009

(30) Foreign Application Priority Data
Jun. 12, 2008 (DE) .......................... 10 2008 002 397

(51) Int. Cl.
A61F 2/06 (2006.01)
(52) U.S. Cl. ...................................... 623/1.42; 623/1.22
(58) Field of Classification Search ......... 623/1.15–1.48
See application file for complete search history.

(56) References Cited

U.S. PATENT DOCUMENTS

| 5,500,013 | A * | 3/1996 | Buscemi et al. ............. 623/1.22 |
| 6,071,305 | A * | 6/2000 | Brown et al. ............... 623/1.43 |
| 6,358,276 | B1 * | 3/2002 | Edwin ...................... 623/1.42 |
| 7,279,175 | B2 * | 10/2007 | Chen et al. .................... 424/423 |
| 2004/0133269 | A1 * | 7/2004 | Bruckheimer et al. ...... 623/1.36 |
| 2004/0236412 | A1 * | 11/2004 | Brar et al. ................... 623/1.31 |
| 2006/0064157 | A1 | 3/2006 | Shanley |
| 2006/0166270 | A1 | 7/2006 | Vogels et al. |
| 2007/0270939 | A1 | 11/2007 | Hood et al. |
| 2007/0288086 | A1 * | 12/2007 | Kalmann et al. ............. 623/1.24 |
| 2008/0033531 | A1 | 2/2008 | Barthel et al. |

FOREIGN PATENT DOCUMENTS

| DE | 10 2006 038232 | 2/2008 |
| EP | 0 344 939 | 12/1989 |
| WO | WO 96/39098 | 12/1996 |
| WO | WO 97/14471 | 4/1997 |
| WO | WO 98/23228 | 6/1998 |
| WO | WO2004/044602 | 5/2004 |
| WO | WO2005/077305 | 8/2005 |
| WO | WO 2005/123044 | 12/2005 |
| WO | WO 2007/137802 | 12/2007 |

OTHER PUBLICATIONS

German Patent Office, Search Report for Priority German Application No. 10 2008 002 397.3, Issued Feb. 27, 2009.
European Patent Office, Search Report for related European Application No. 09 16 0150, Issued Jun. 21, 2010.

* cited by examiner

*Primary Examiner* — Suzette J Gherbi
(74) *Attorney, Agent, or Firm* — Greer, Burns & Crain, Ltd.

(57) ABSTRACT

The invention relates to an implantable device for local release of at least one drug at a predefined location in a natural cavity having a wall in the body of a mammal, characterized by at least one drug reservoir, which can be affixed in the cavity, the drug reservoir and/or a drug outlet being arranged at a distance from the wall, such that the at least one drug is released at a distance from the wall.

19 Claims, 4 Drawing Sheets

IMPLANTABLE DEVICE

The invention relates to an implantable device according to the preambles of the independent claims.

In medical technology, implantable devices for local release of drugs at a predefined location in a natural body cavity in a mammal, e.g., in a tissue channel, are widely known. The existing proposed approaches are often unable to introduce sufficiently large quantities of drug at defined regions. Difficulties often arise when using two or more different drugs at the same time, for example. Other proposed approaches relate to a fully degradable vascular supporting body with a high drug load. One problem here is that such vascular stents can cause substantial adverse effects locally in the tissue of the vascular wall due to direct contact of the drug-releasing implant parts with the vascular wall, in particular when cytostatic drugs are being released. Such adverse effects may necessitate complex treatments for prevention and reduction of adverse effects.

The object of the present invention is to provide an implantable device capable of delivering large quantities of one or more drugs to a natural body cavity of a mammal, e.g., to a tissue channel, in particular to an arterial vessel, without thereby burdening the wall of the cavity with the drug in the area of the implantable device.

This object is achieved according to the present invention through the features of the independent claims. Favorable embodiments and advantages of the invention are derived from the other claims and the description.

With an inventive implantable device, at least one reservoir of drag is provided, such that the drug reservoir can be affixed in the cavity and the drug reservoir and/or a drug outlet arranged at a distance from the wall, such that the drug is released as a distance from the wall. An alternative inventive implantable device relates to a drug reservoir having a drug outlet, such that the drug outlet is formed by a perforated sheath of a coil wound in the form of a spiral or helical coil. These proposed approaches advantageously allow implantation of large quantities of drug in predetermined regions of a body cavity, in particular of arteries, without creating a burden of the drug on the vascular wall. Thus adverse effects such as inflammation or necroses can thus be prevented advantageously. In the following discussion, the cavity is referred to only as an artery and/or an arterial vessel.

The implantable device is introduced into an arterial vessel by a known insertion system (SDS) using a catheter. The implant is preferably designed as an implantable supporting body, e.g., a stent, which is introduced into the arterial vessel. In one variant, a structure comprising a helical or spiral-shaped tube (coil), which is inserted into the arterial vessel, may also be provided as the implantable supporting body. The implantable supporting body is preferably made of nitinol. The implantable supporting bodies may advantageously serve as fixation elements for a drug reservoir, whereby the drug outlet is especially preferably arranged centrally in the artery. An unfavorable burden of the drugs being released on the vascular wall can thus be avoided. If more than one drug is required for treatment, then the drug reservoir may comprise multiple drug containers.

The drug reservoir may also consist of several parts with different drugs. The drug reservoir preferably has a fixation element designed as a stent and/or a coil, preferably on at least one end, and especially preferably embodied as a stent and/or a coil, so that the drug outlet is held in the defined position within the vessel and is supported against the walls of the cavity. The drug reservoir may preferably be formed from the coil itself having a proximal end and a distal end, such that the proximal end is in contact with the inside wall of the vessel. The proximal end of the coil is advantageously designed to be in contact with the vascular wall without having any effect on the hemodynamics. At its distal end, the coil is designed to protrude approximately into the center of the arterial vessel, whereby the distal end is provided for release of the drug substance by diffusion. The more central the distal end position, the more advantageous it is.

The drug reservoir is especially preferably held at both of its ends with the help of the fixation elements, preferably being affixed coaxially. The drug reservoir is advantageously held centrally in the bloodstream, either at one or both ends, by coiling or by means of stent-like supporting bodies. The coils and/or stents are especially preferably self-expanding and thus adjust themselves at a defined location in the vessel.

In an advantageous variant, the fixation element may itself form the drug outlet. The coil or the stent itself may serve as the drug reservoir, especially preferably having a porous sheathing. The release of the drug may take place by diffusion through a capillary action, whereby again a local burden on the internal vascular wall due to the drug being released can advantageously be avoided. The drug can advantageously be transported out of the drug reservoir with the help of the capillary action and released into the bloodstream without a direct burden on the vascular wall.

In another advantageous variant, the drug may be released through biodegradable materials. The material is preferably formed from a biodegradable polymer or a metal, e.g., stainless steel and tantalum, platinum and nitinol. The drug reservoir in this variant is preferably formed from a multi-layer body of preferably biodegradable materials, whereby the spaces between the layers are filled with the same or different drugs. The drug may advantageously be released after degradation of the layers, whereby an unfavorable burden on the vascular wall is again omitted. If the interspaces are filled with the same drug, the release of the drug may advantageously proceed in a controlled manner by making the drug available for a sufficiently long period of time. Alternatively or additionally, a primarily diffusion-controlled release of one or more drugs from the biodegradable material may take place. The surface of the body may then serve as the drug outlet.

In another variant, the drug reservoir may be formed from a preferably streamlined body made of a polymer, which is loaded with the desired drug. Due to the geometric shape, the polymer body may cause a self-adjustment of the drug-releasing implant part in the middle of the vessel. The body may have fixation wings, such that the fixation wings have small contact areas with the vascular wall and ensure that the implant is suspended in the vessel in a manner that maintains the lumen. The contact area is preferably designed to be linear, especially preferably in the form of a spot. However, there is advantageously a slight input of drug into the vascular wall. As an alternative, the fixation wings may be designed to be drug-free.

The individual variants and embodiments may also be combined in any desired manner. In all the embodiment variants, large quantities of drug, e.g., 5 mg to 10 mg of one or more drugs, may advantageously be delivered to an arterial vessel without thereby burdening the vascular wall in the area of the implant with the drug. Adverse effects may thus be avoided to advantage. In an especially preferred application, the inventive implantable device may be introduced into an arterial vessel just upstream from an organ, e.g., the liver, kidneys, etc., whereby a large quantity of drug can advantageously be introduced into the vessel in a high-flow bloodstream, so that the drug is rapidly dispensed to the target region.

The invention is explained in greater detail below on the basis of exemplary embodiments depicted in drawings, which show schematically:

Figure 1:
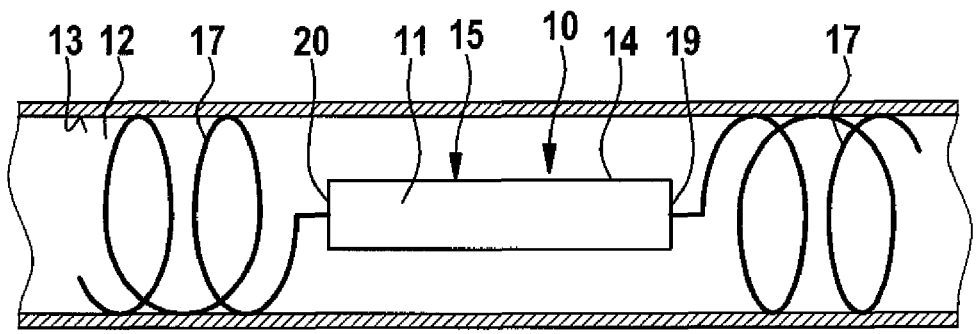
FIG. 1 shows a section through a cavity in the form of an arterial vessel with a preferred embodiment of an implantable device for local release of at least one drug into the vessel at a predefined location, whereby the implantable device is formed from a drug reservoir, which is affixed at both ends by a supporting body designed as a coil.

Elements that are functionally the same or have the same effect are each labeled with the same reference numerals in the figures. The figures are schematic diagrams of the invention. They illustrate nonspecific parameters of the invention. In addition, the figures show only typical embodiments of the invention and should not limit the invention to the embodiments shown here.

FIG. 1 shows in a schematic diagram a longitudinal section through a cavity embodied as an arterial vessel 12 with a preferred embodiment of an implant 10 for local delivery of at least one drug 11 at a predetermined location in the vessel 12. The implant 10 comprises a drug reservoir 14, which is connected at each of its two ends 19 and 20 to two supporting bodies designed as coils 17. The coil 17 is a screw-shaped or spiral coiled tube, which is arranged in the vessel 12, so that it is coaxially situated with respect to the vessel 12 and the drug reservoir 14. The coils 17 are especially preferably self-expanding and thus automatically affix themselves after being introduced into the vessel 12, such that the coils 17 are in contact with the interior vascular wall 13 at their periphery. The drug reservoir 14 is filled with at least one drug 11, which is introduced into the vessel 12 by diffusion through capillary action. The drug outlet 15 is formed by the surface of the drug reservoir 14. In particular, the drug reservoir 14 is affixed in the vessel 12, so that the drug reservoir 14 and thus the drug outlet 15 are arranged at a distance from the vascular wall 13. Loading of the vascular wall 13 and/or the lumen with the drug 11 is thus advantageously avoided.

Figure 2:
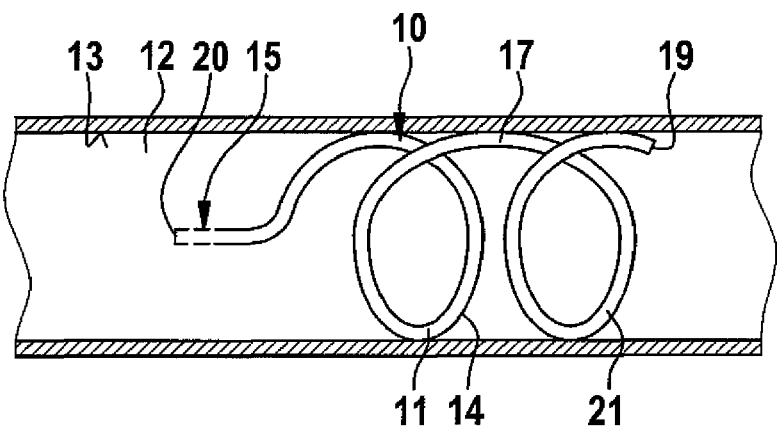
FIG. 2 shows a section through the arterial vessel with another preferred variant according to another independent aspect of the invention.

FIG. 2 shows a another preferred variant according to another independent aspect of the present invention, whereby the implantable device 10 is designed as a coil 17, which is introduced into an arterial vessel 12. The coil 17 serves as a fixation element 21 and at the same time forms the drug reservoir 14 with a drug outlet 15. The coil 17 has a proximal end 19 and a distal end 20, whereby the proximal end 19 is arranged in the area of the inside wall 13 of the arterial vessel 12. The coil 17 is arranged with its distal end 20 approximately centrally in the cavity 12. The distal end 20 forms the drug outlet 15, which is arranged centrally in the vessel 12.

Figure 3:
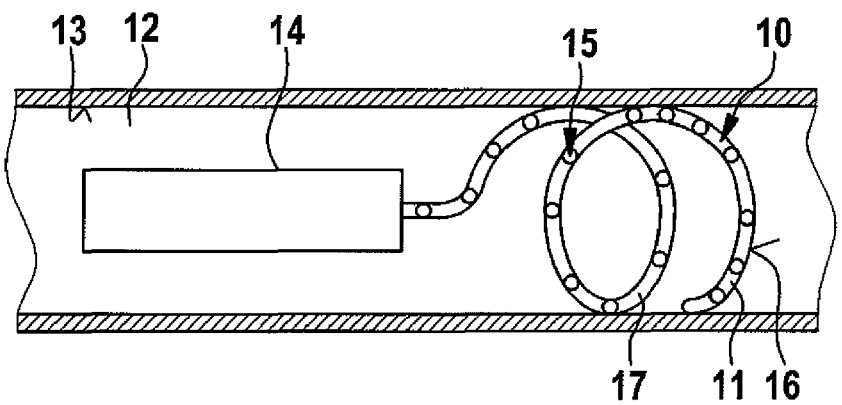
FIG. 3 shows a sectional diagram through the arterial vessel with a preferred alternative implantable device which is formed from a drug reservoir and a coil with a perforated sheath.

FIG. 3 shows another variant of a device 10, which is implantable in an arterial vessel 12 and comprises a drug reservoir 14 connected to a coil 17. The drug outlet 15 is formed by a porous sheath 16, in particular a perforated sheath on the coil 17. The drug 11 diffuses through the perforated sheath 16 of the coil 17 into the vessel 12 without thereby loading the wall 13 of the vessel 12 locally with the drug 11.

Figure 4:
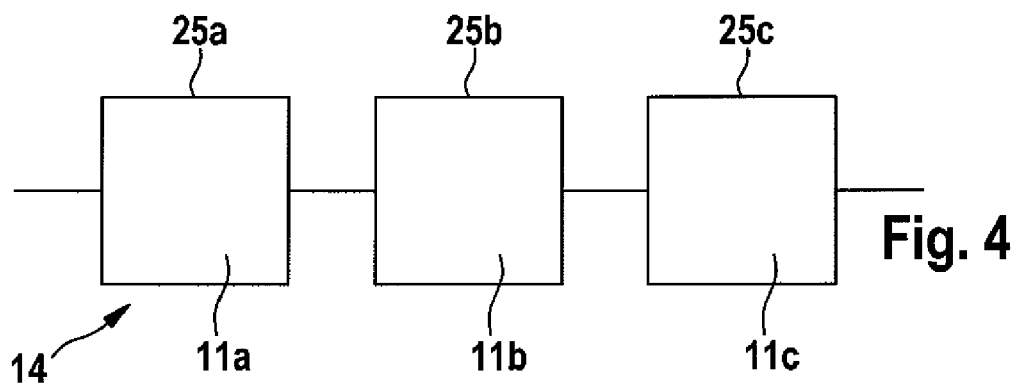
FIGS. 4 to 9 show other variants of an implantable device.

As diagrammed schematically in FIG. 4, the drug reservoir 14 may consist of several drug containers 25a, 25b, 25c, different drugs 11a, 11b, 11c being introduced into each. These may be introduced into the blood vessel 12 as described in conjunction with the other figures.

Figure 5:
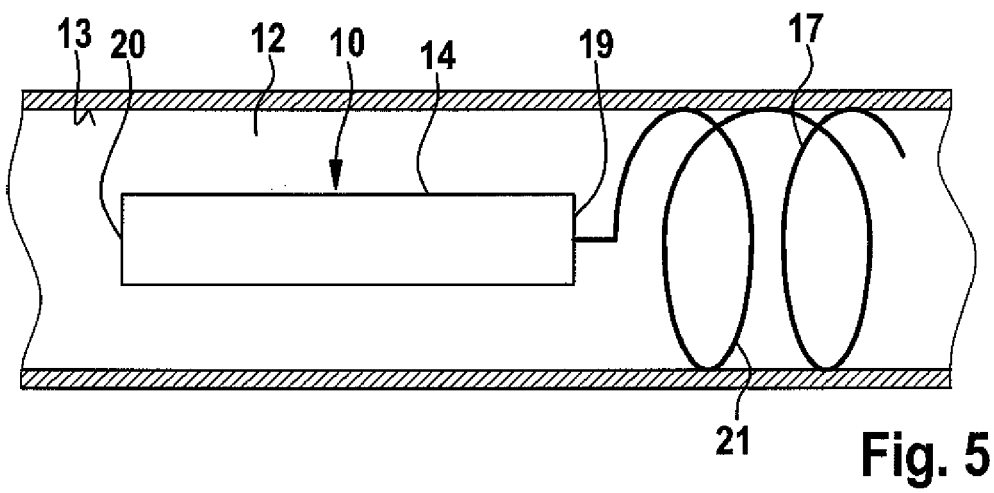

The implantable device 10 illustrated in FIG. 5 is formed from a drug reservoir 14, which is connected at one of its ends 19, 20 to a coil 17. The coil 17 is preferably designed to be self-expanding and is supported on the inside wall 13 of the vessel 12 in an end position and is thereby secured. The coil 17 serves as a fixation element 21 for the drug reservoir 14, which is especially preferably held centrally in the vessel 12.

Figure 6:
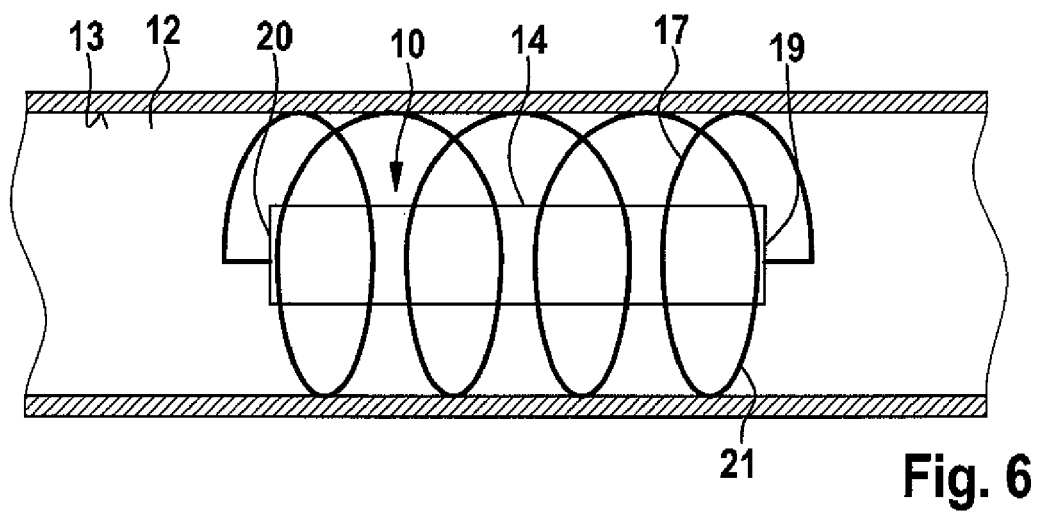
Figure 7:
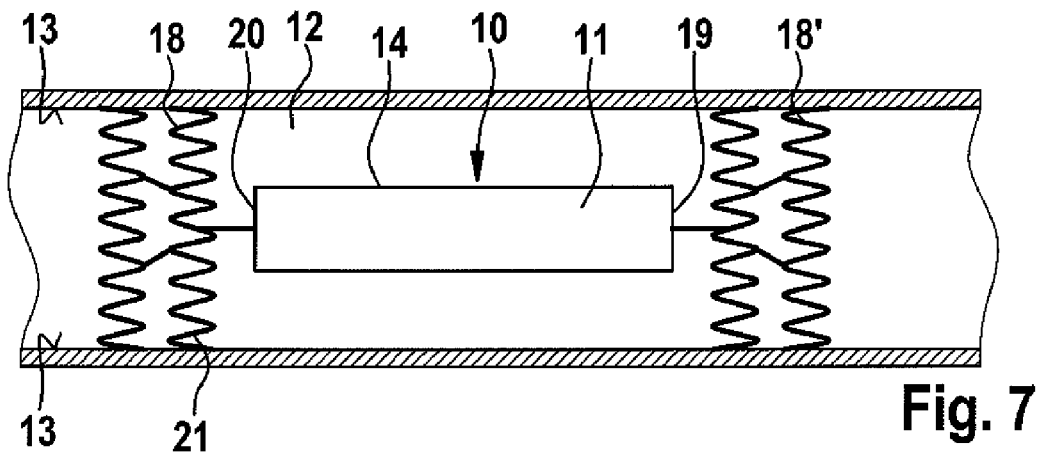
Figure 8:
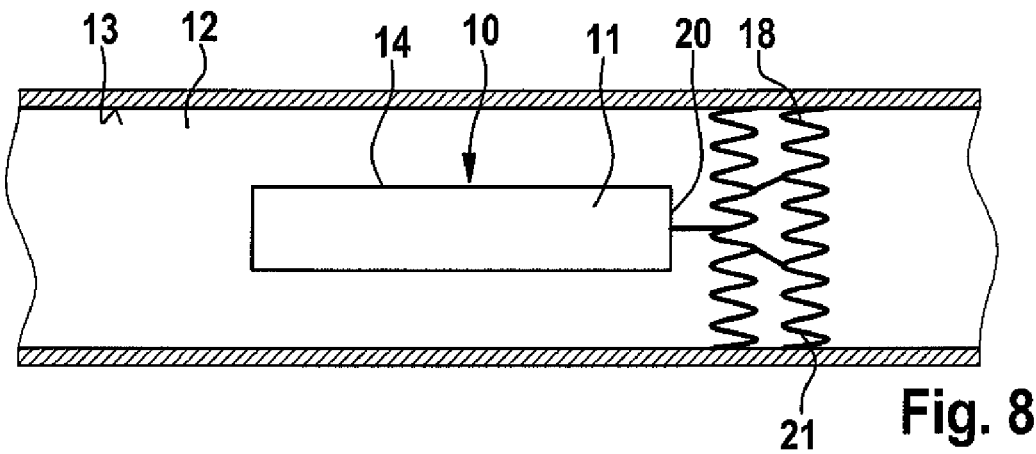
Figure 9:
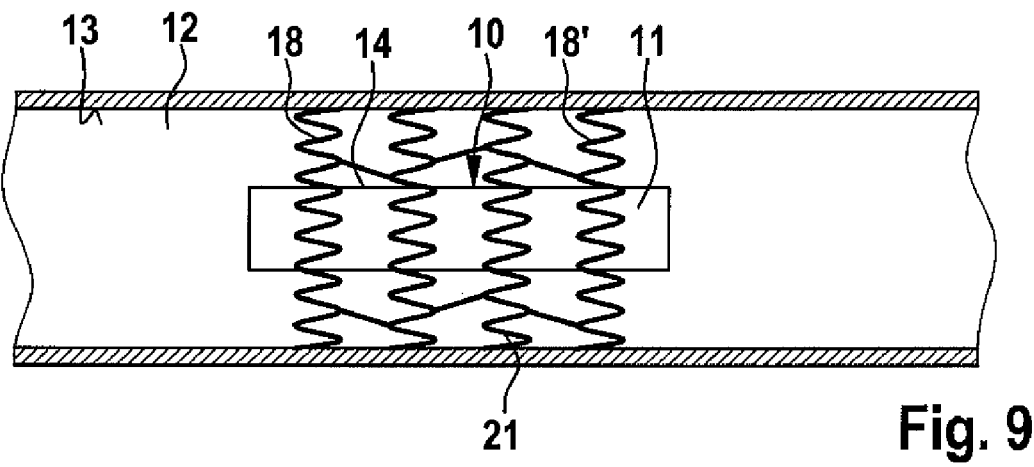

FIG. 6 shows the drug reservoir 14 connected to a coil 17, so that it is affixed coaxially with the coil 17 in the vessel 12. The drug reservoir 14 is designed as an elongated cylindrical body, which is connected at its two ends 19, 20 to the coil 17 and is arranged coaxially inside the coil 17. FIG. 7 shows another variant of a preferred implantable body 10, whereby a drug reservoir 14 has a fixation element 21 designed as a stent 18, 18' on both ends 19, 20. The stents 18, 18' are advantageously self-expanding and are affixed automatically in the arterial vessel 12 in a defined end position. In an alternative embodiment according to FIG. 8, the drug reservoir 14 is connected to a stent 18, preferably at a distal end 20. The stent 18 serves as a fixation element 21 for the drug reservoir 14, which is held in a central area of the vessel 12. In another variant according to FIG. 9, a drug reservoir 14 is affixed coaxially with the help of a fixation element 21 designed as a stent 18, 18'. The drug 11 introduced into the drug reservoir 14 can be released into the vessel 12 by diffusion through capillary action without having any negative effect on the vascular wall 13 or the lumen. In one variant, the drug 11 can be released into the vessel 12 by degradation of biodegradable materials that form a sheathing of the drug reservoir 14. For example, polymer or metal may be used as biodegradable materials.

Figure 10A:
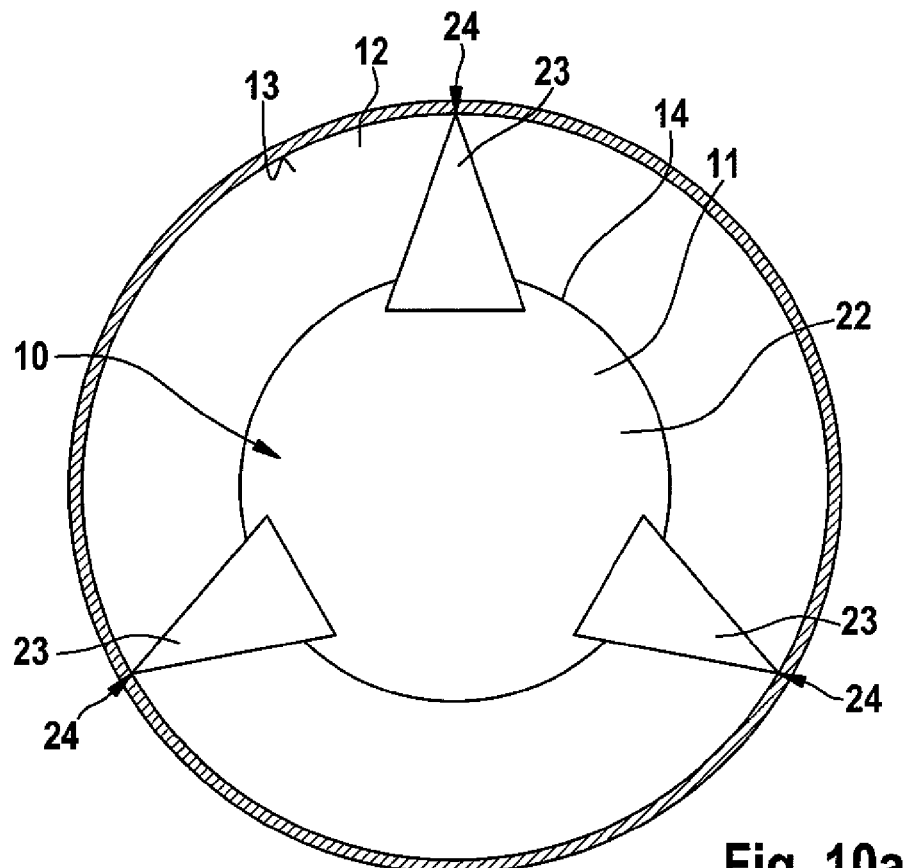
FIGS. 10a, 10b show an alternative preferred embodiment of an implantable device embodied as a self-adjusting polymer body in the arterial vessel shown here in a cross section (FIG. 10a) and in a longitudinal section (FIG. 10b).
Figure 10B:
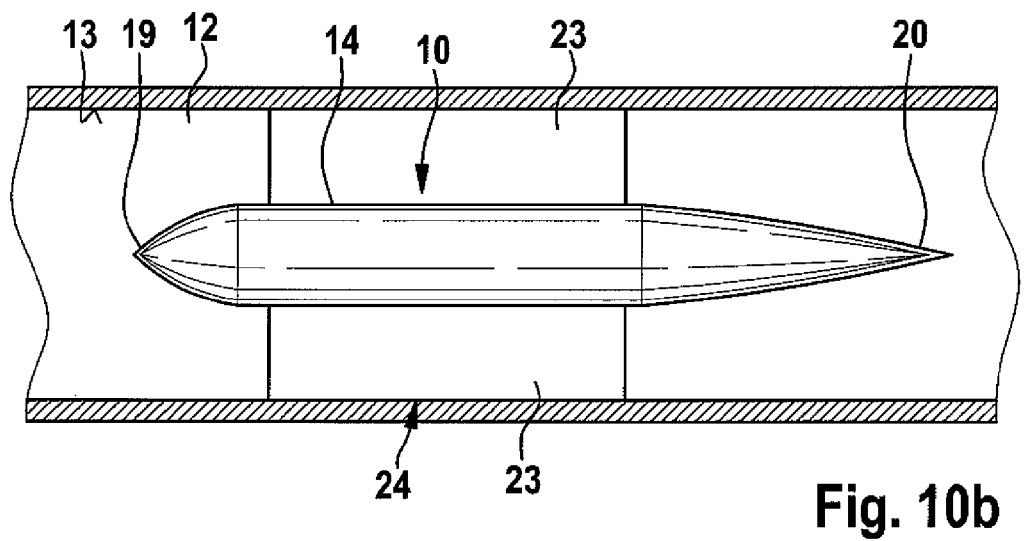

In an especially preferred variant according to FIGS. 10a, 10b, the drug reservoir 14 is formed by a multi-layer polymer body 22 made of biodegradable materials, whereby spaces between the layers, which are not shown individually in greater detail, are filled with the at least one drug 11. After degradation of the layers, the drug 11 can be released successively into the arterial vessel 12. Alternatively or additionally, one or more drugs may be released from the biodegradable material in a primarily diffusion-controlled process.

FIG. 10a shows a cross section through the polymer body 22 arranged in an arterial vessel 12; FIG. 10b shows a longitudinal section through the polymer body 22. The polymer body 22 is preferably designed to be streamlined and has a proximal end 19 and a distal end 20. The polymer body 22 containing the drug is preferably held by fixation wings 23 in a central position in the vessel 12 in the area of its proximal end 19. The fixation wings 23 result in a self-adjustment of the streamlined polymer body 12 in a central area of the arterial vessel 22. The fixation wings 23 have a small contact area 24, preferably designed to be linear or in the form of a spot on the wall 13 and thus ensure suspension of the implantable body 10 in the vessel 12 in such a way that it preserves the lumen. If the drug 11 acts on the fixation wings 23, a small amount of drug is input into the wall 13 due to the small contact area 24 with the wall 13. Alternatively, the fixation wings 23 may also be designed to be drug-free.

What is claimed is:

1. An implantable device for local release of at least one drug at a predetermined location in a natural cavity with a wall in the body of a mammal, characterized by at least one drug reservoir with a drug outlet, the reservoir configured as an elongated cylindrical body that is held centrally in the cavity with no portion contacting the cavity wall, whereby the drug outlet is at least partially formed by a perforated sheath of a spiral or helical coil that extends from the cylindrical body, a portion of the spiral or helical coil contacting the wall to thereby hold the cylindrical body in place centrally in the cavity.

2. An implantable device for local release of at least one drug at a predefined location in a natural cavity having a wall in the body of a mammal, characterized by at least one drug reservoir configured as an elongated cylindrical body and having a drug outlet for communicating the drug from the reservoir, the reservoir configured to be affixed in the cavity by a fixation element on at least one end of the drug reservoir supported against the walls of the cavity and configured to hold the elongated cylindrical reservoir body in position near the middle of the cavity wherein the entirety of the elongated cylindrical body is separated by some distance from the cavity wall whereby no portion of the cylindrical body contacts the cavity wall, such that all of the at least one drug is released at a distance from the wall.

3. The implantable device according to claim 2, characterized in that the fixation element forms the drug outlet.

4. The implantable device according to claim 2, further characterized in that the fixation element is designed as at least one of the drug reservoirs.

5. The implantable device according to claim 2, characterized in that the drug reservoir consists of several drug containers, a first of the several containers contained in the elongated cylindrical body having a first end, and a second of the several containers contained in the fixation element having a first end connected to the cylindrical body first end, the fixation element having a second end engaging the cavity wall.

6. The implantable device according to claim 2, wherein the fixation element comprises a stent that engages the cavity wall at multiple locations.

7. The implantable device according to claim 2, wherein the fixation element is coil or spiral shaped, characterized in that the drug reservoir is secured coaxially with the fixation element.

8. An implantable device for local release of at least one drug at a predefined location in a natural cavity having a wall in the body of a mammal, characterized by at least one drug reservoir formed from a coil having a proximal end and a distal end, the coil proximal end in contact with the wall of the cavity, the coil distal end approximately at the center of the cavity, and whereby the distal end defines a drug outlet for communicating the drug from the reservoir, the reservoir configured to be affixed in the cavity, whereby the drug reservoir and or an entire drug outlet is arranged at a distance from the wall, such that all of the at least one drug is released at a distance from the wall.

9. An implantable device for local release of at least one drug at a predefined location in a natural cavity having a wall in the body of a mammal, characterized by at least one drug reservoir having a drug outlet for communicating the drug from the reservoir and configured for releasing the at least one drug by diffusion into the cavity by capillary action, the reservoir configured to be affixed in the cavity whereby the entire drug outlet is arranged at a distance from the wall such that all of the at least one drug is released at a distance from the wall.

10. The implantable device according to claim 8, characterized in that the at least one drug can be released into the cavity by biodegradable materials.

11. The implantable device according to claim 8, characterized in that the drug reservoir is formed from a multi-layer body of biodegradable materials; spaces between the body layers filled with the at least one drug, and the drug can be delivered successively into the cavity after degradation of the layers.

12. An implantable device for local release of at least one drug in a natural cavity having a wall in the body of a mammal, comprising at least one drug reservoir, configured to be affixed in the cavity, whereby the drug reservoir and/or a drug outlet is arranged at a distance from the wall, such that the at least one drug is released at a distance from the wall, and wherein the drug reservoir has a polymer body, which produces a self-adjustment of the drug reservoir in the middle of the cavity due to its geometric shape.

13. The device according to claim 12, characterized in that the polymer body has at least two fixation wings, which have a small contact area with the wall of the cavity.

14. The device according to claim 2, wherein the fixation element is spiral shaped.

15. The device according to claim 14 and further comprising a second spiral shaped fixation element connected to the elongated body, each of the first and second spiral fixation elements having distal ends engaging the cavity wall.

16. The device according to claim 14 wherein the reservoir body has a cylindrical shape with opposing first and second ends, the first spiral shaped fixation element has a first spiral end connected to the reservoir body first end, and the first spiral shaped fixation element has a distal second end connected to the opposing second end of the cylindrical body, the entirety of the cylindrical body fixed between the first and second distal ends of the spiral fixation element and held coaxially with the spiral fixation element in the middle of the cavity.

17. The device according to claim 7 wherein the cylindrical body is held coaxially within the coil or spiral shaped fixation element.

18. The device according to claim 5 and further comprising a second fixation element having a first end connected to a second end of the cylindrical body, the second fixation element having a second end engaging the cavity wall to hold the cylindrical body in place in the cavity entirely separated from the cavity wall.

19. A device for implanting in a mammal cavity to deliver at least one drug to the cavity, the cavity having a wall, the device comprising:
   at least one elongated reservoir containing the at least one drug;
   at least one generally spiral shaped fixation element having a first end connected to the elongated reservoir, the fixation element engaging the cavity sidewall and holding the elongated reservoir in place approximately at the center of the cavity and entirely separated from the cavity wall; and,
   a drug outlet communicating with the reservoir and positioned in a location away from the cavity wall whereby all of the at least one drug is released at a location some distance from the cavity wall to avoid direct loading of the cavity wall with drug.

* * * * *